United States Patent [19]

Nomoto et al.

[11] Patent Number: 4,484,580
[45] Date of Patent: Nov. 27, 1984

[54] SUTURING INSTRUMENT FOR SURGICAL OPERATION

[75] Inventors: Reishi Nomoto; Masayoshi Takahashi, both of Kanagawa; Yoshikazu Ebata, Tokyo, all of Japan

[73] Assignee: Janome Sewing Machine Co., Ltd., Tokyo, Japan

[21] Appl. No.: 335,599

[22] Filed: Dec. 30, 1981

[30] Foreign Application Priority Data

Mar. 20, 1981 [JP] Japan .................. 56-38341[U]

[51] Int. Cl.³ .......................................... A61B 17/04
[52] U.S. Cl. ................................................. 128/340
[58] Field of Search ............... 128/340, 4; 112/169; 223/104; 242/99

[56] References Cited

U.S. PATENT DOCUMENTS

| | | | |
|---|---|---|---|
| 999,641 | 8/1911 | Fuerst | 242/99 |
| 2,327,353 | 8/1943 | Karle | 128/340 |
| 2,365,647 | 12/1944 | Ogburn | 128/340 |
| 2,393,911 | 1/1946 | Karle | 128/340 |
| 2,957,264 | 10/1960 | Ruff | 242/99 |
| 3,638,653 | 2/1972 | Berry | 128/340 |

FOREIGN PATENT DOCUMENTS

| | | | |
|---|---|---|---|
| 8702 | of 1895 | United Kingdom | 223/104 |
| 598866 | 2/1948 | United Kingdom | 242/99 |
| 1264796 | 2/1972 | United Kingdom | 112/169 |

Primary Examiner—Michael H. Thaler
Attorney, Agent, or Firm—Michael J. Striker

[57] ABSTRACT

A suturing instrument for surgical operations having a needle holder with a needle and a shuttle holder with a shuttle is provided with an arrangement for controlling the amount of suturing thread drawn out of a bobbin loaded with the thread. The device includes a grooved flange on the bobbin and a spring-biased braking lever turnable in a housing of the instrument and engageable with a respective groove of the flange to maintain the optimum amount of the thread supplied from the bobbin to the needle and the shuttle and to form up the constant stitches during operation.

4 Claims, 12 Drawing Figures

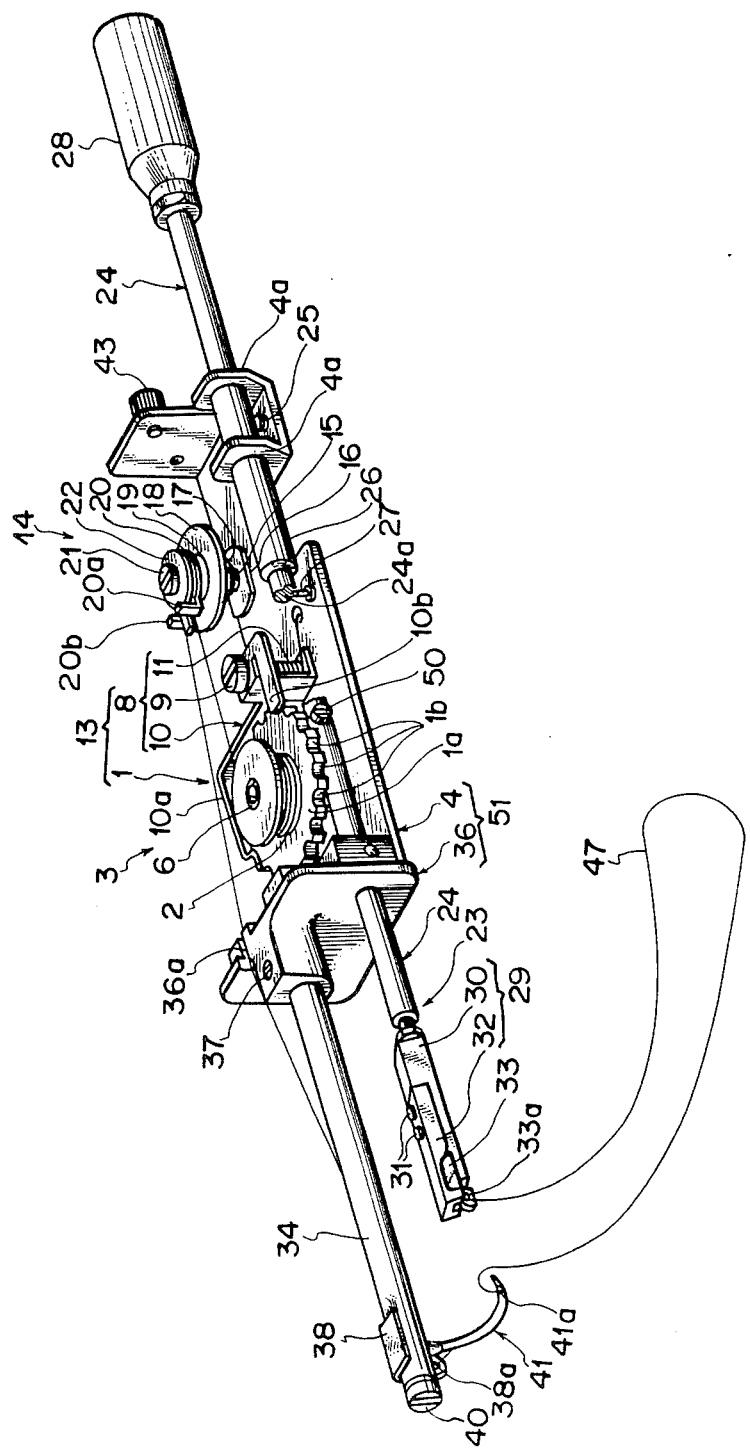
FIG_1

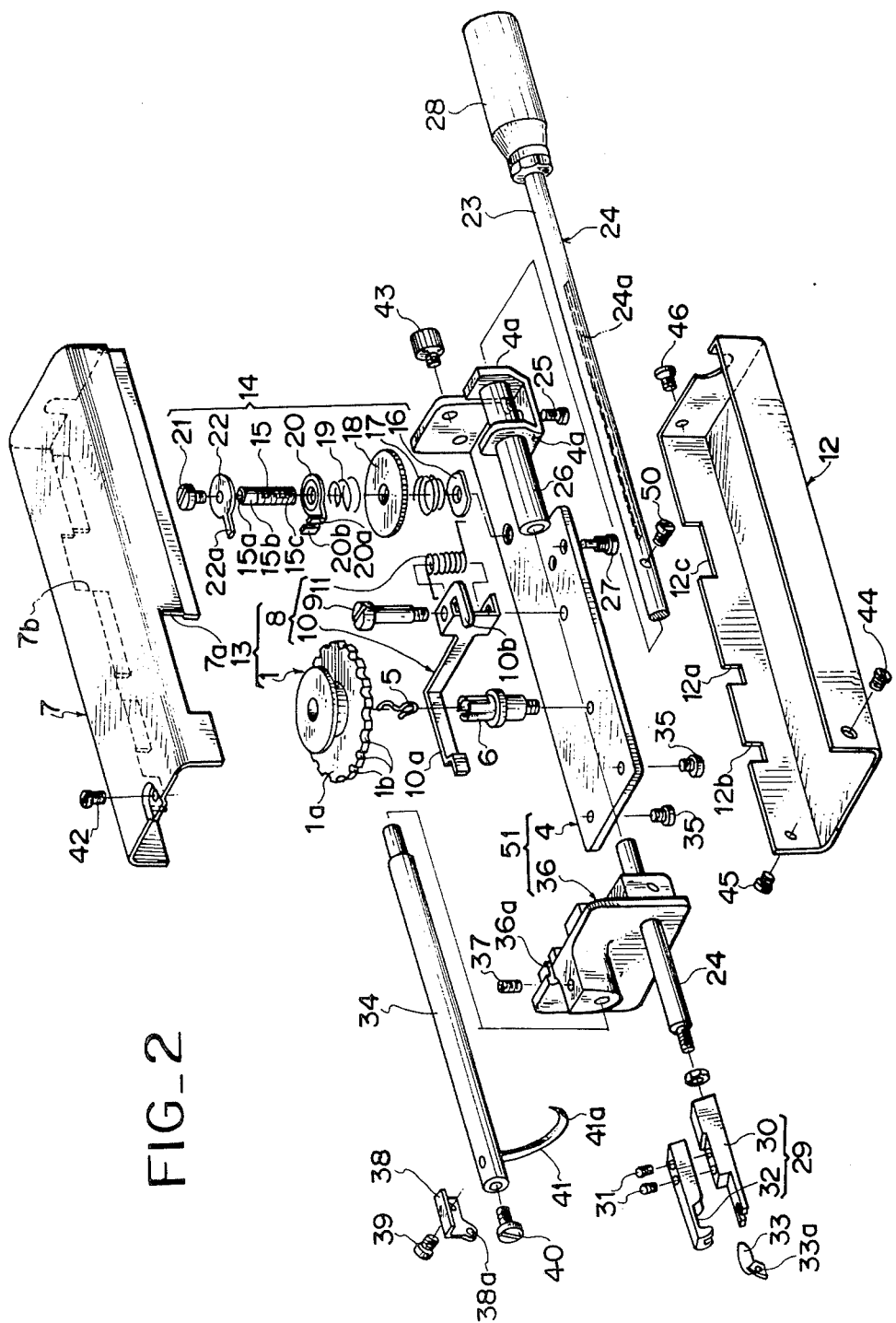
FIG_2

FIG_3
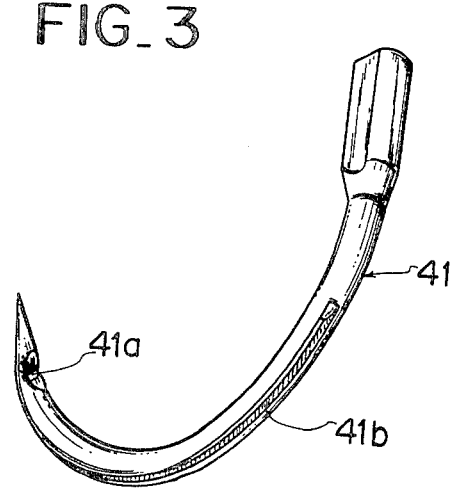
FIG_4
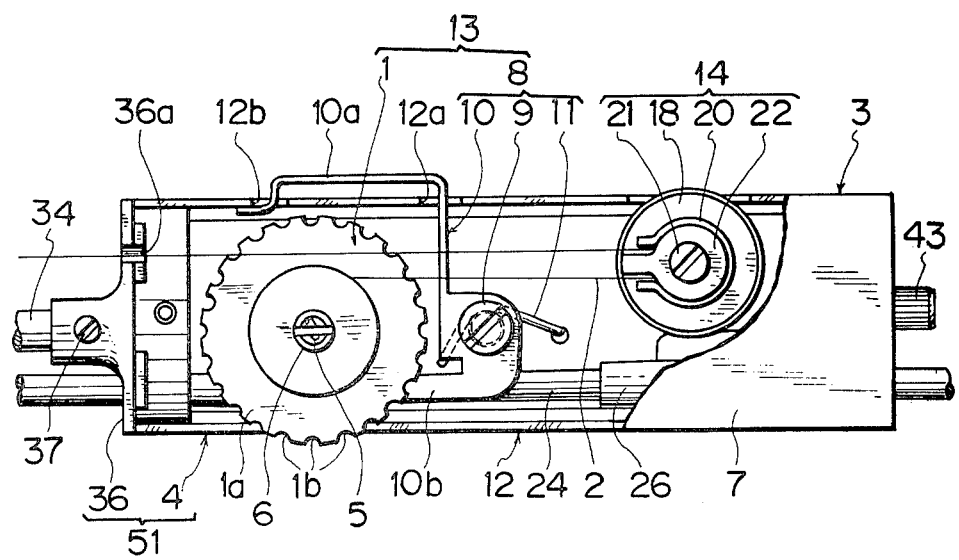

FIG_5
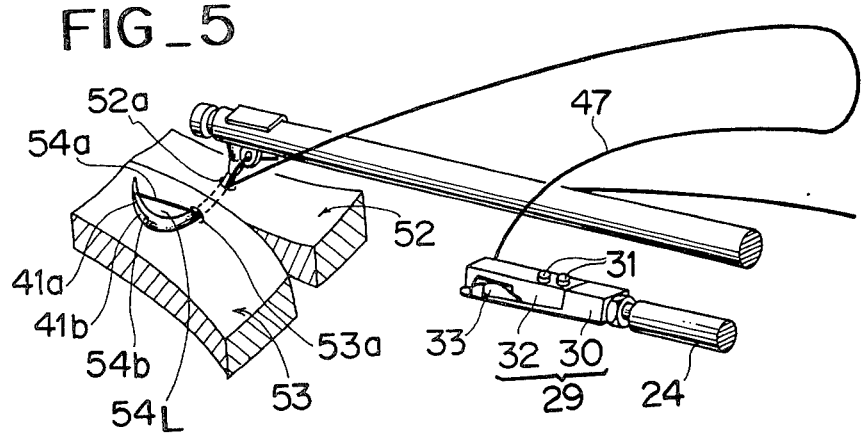
FIG_6
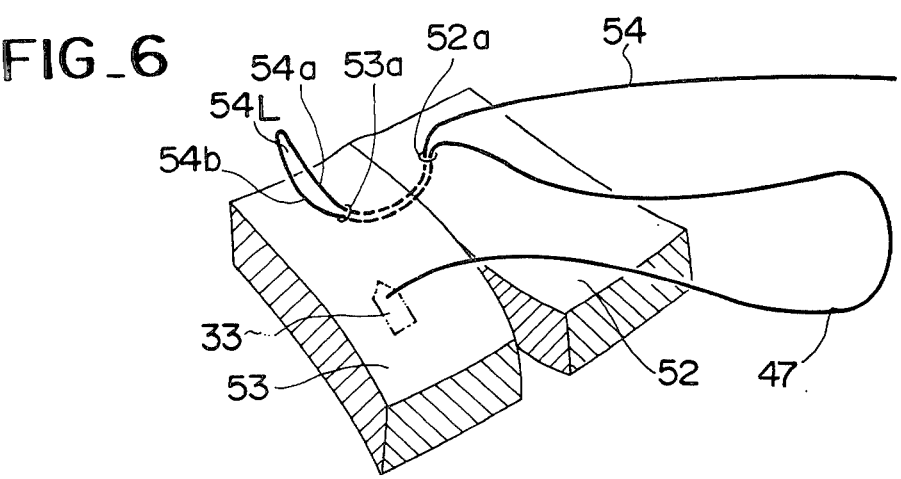
FIG_7
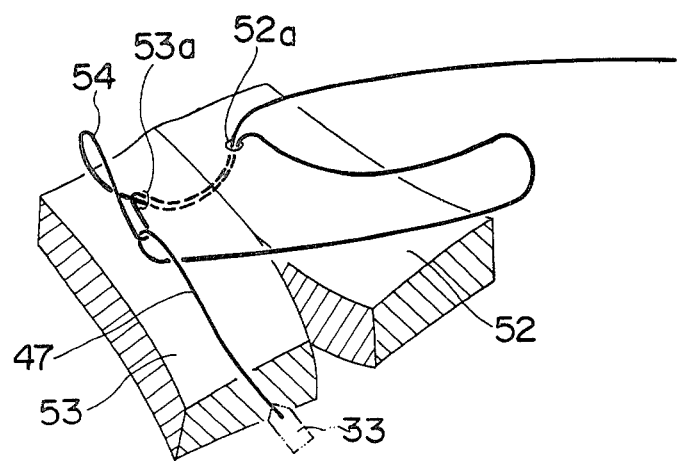

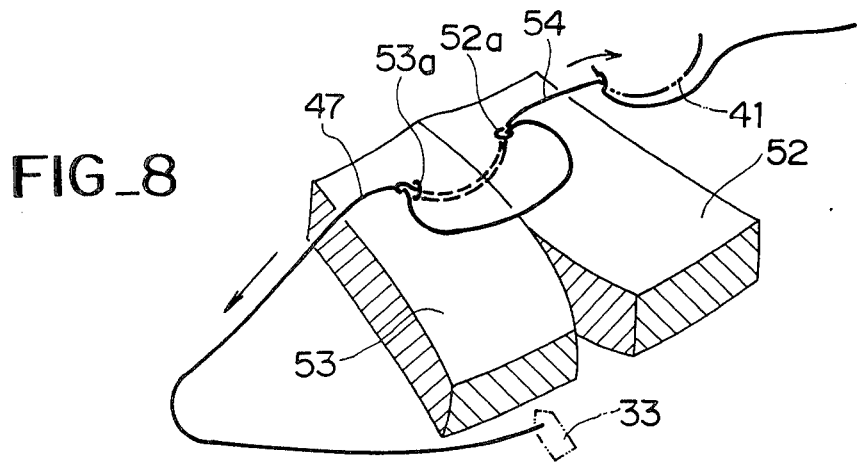
FIG_8
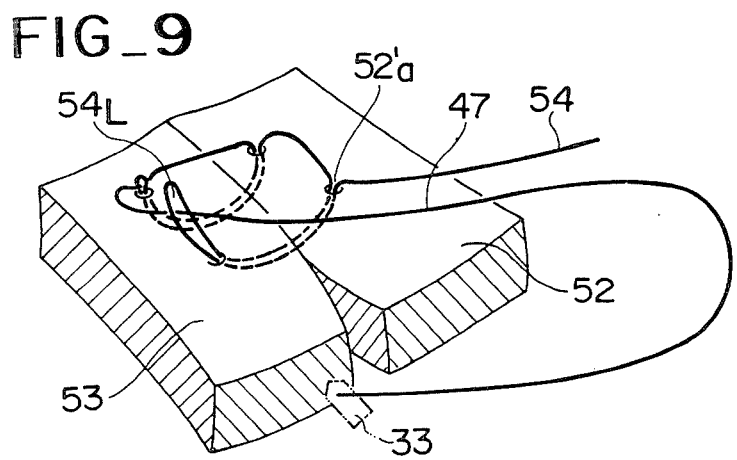
FIG_9
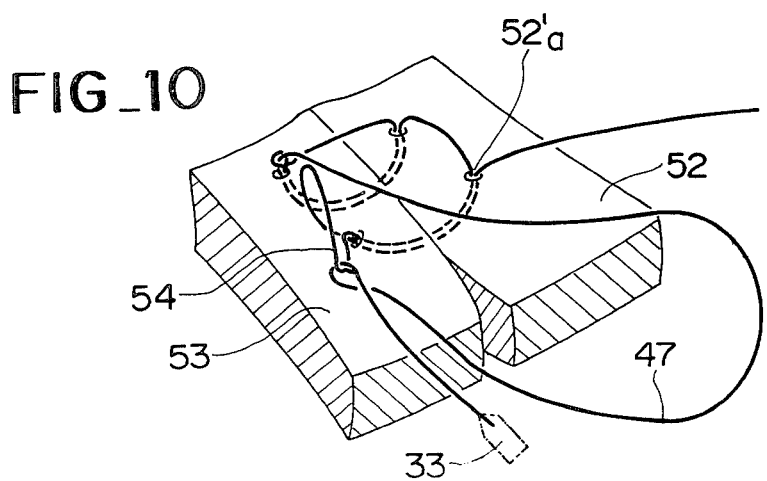
FIG_10

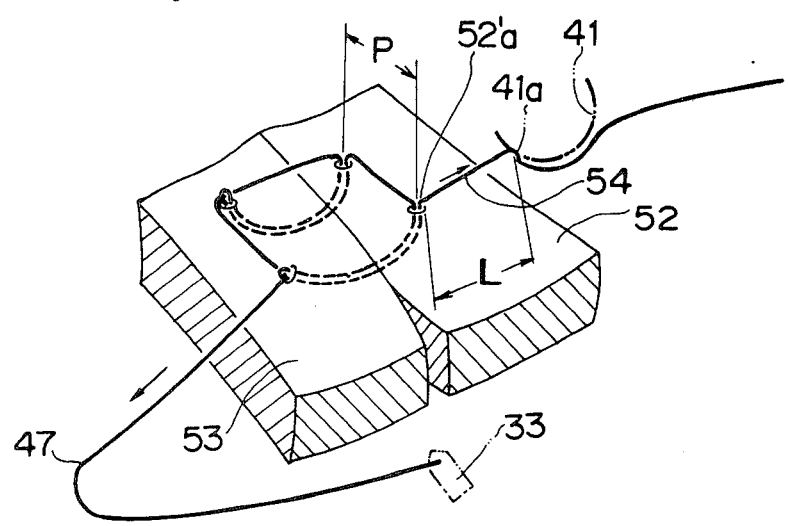
FIG_11
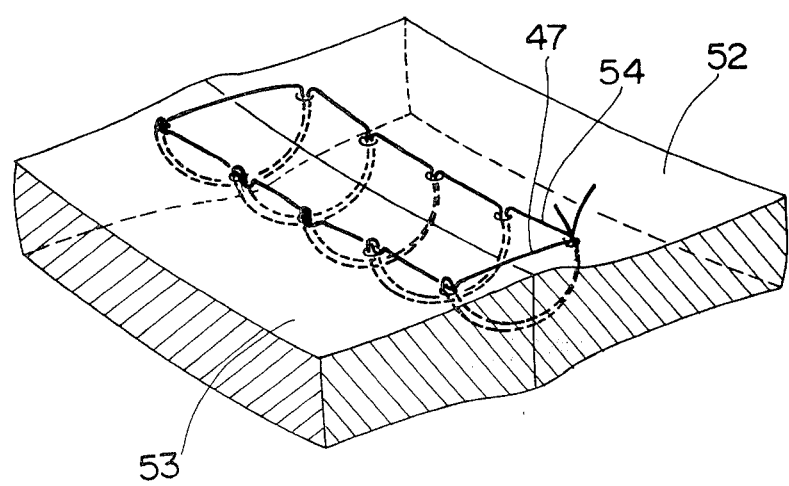
FIG_12

SUTURING INSTRUMENT FOR SURGICAL OPERATION

BACKGROUND OF THE INVENTION

The invention relates to a suturing instrument for surgical operations, which crosses a suturing thread combined to a shuttle and a suturing thread combined to a curved needle to form lock stitches for stitching up the wound or the cut out flesh.

It has been a conventional practice to carry out the suturing operation at the incised parts of the patient by a curved needle formed with a needle eye at the shank thereof, which is held by a holder handled by an operator with a thread passed through the needle eye of the curved needle. Thus, the curved needle is inserted into a part to be sewn up and then the needle is released to manually form up a knotted seam per stitch; therefore the suturing operation has required a long time and a physically heavy burden on the side of the operator as well as the patient.

For shortening the suturing time, there has been a conventional staple type instrument which combines the human part to be sutured by means of metallic staples such as silver or others. According to said combining instrument, the metallic staples will remain in the human body, and these staples make unclear the images of X-rays when the process after the operation is observed, or those as foreigners give psychological bad influence to the patient.

SUMMARY OF THE INVENTION

In the suturing instrument for the surgical operation which crosses the suturing thread combined to the shuttle and the other thread combined to the curved needle, the present invention is to operate the suturing instrument outside thereof for supplying and winding the thread in order to maintain the optimum supplying amount of the thread and form up the constant stitches.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWINGS

FIG. 1 is a perspective view of a suturing instrument according to the invention, with a cover taken off;

FIG. 2 is a perspective view of the dissembled suturing instrument;

FIG. 3 is a perspective view of the curved needle;

FIG. 4 is a plan view of element part of the suturing instrument;

FIG. 5 is a perspective view showing a suturing condition;

FIGS. 6 to 11 are perspective views showing the suturing process after a first penetration of the curved needle in relation between the needle thread and the shuttle thread;

FIG. 7 is a view showing a condition of crossing the shuttle thread into a loop of the needle thread;

FIG. 8 is a view showing a condition of tightening the needle thread and the shuttle thread;

FIG. 9 is a view showing a condition between the needle thread and the shuttle thread at second penetration of the curved needle;

FIG. 10 is a view showing a condition of crossing the shuttle thread into the loop of the thread needle;

FIG. 11 is a view showing a condition of tightening the needle thread and the shuttle thread; and FIG. 12 is a perspective view showing a condition of completing the suturing operation.

DETAILED DESCRIPTION OF THE INVENTION

The present invention will be explained in reference to actual embodiment. In FIGS. 1 and 2, the reference numeral 1 is a thread supply member which is detachably attached on a thread standing axis 6 having a spring 5 secured on a machine frame 4. The thread supply member 1 is formed with a plurality of grooves 1b on a flange 1a thereof along an outer circumference.

The flange 1a partially exposes through a cutout 7a of the cover 7 in the present embodiment, when the thread supply member 1 is attached to the thread standing axis 6. The numeral 8 is a control mechanism, which is composed of a braking axle 9 secured to the machine frame 4, a braker 10 which is formed with an operating part 10a at one side and formed with an engaging portion 10b at the other side, and a braking spring 11 which biases the braker 10 in the clockwise direction around the braking axle 9 in FIG. 4, and engages the engaging portion 10b into the groove 1b formed in the flange 1a of the thread supply member 1. The operating portion 10a of the braker 10 exposes through a cover 12 of the suturing instrument, i.e., the cutouts 12a and 12b of the cover 12 in the present embodiment. The thread supply member 1 may be angularly rotated outside of the suturing instrument via the flange 1a by the engagement of the engaging portion 10a into the groove 1b of the flange 1a, and the biasing force of the braking spring 11 is selected so that the thread supply member is not rotated against the force acting through the suturing thread 2 at tightening it. A thread supply control device 13 is composed of the thread supply member 1 and the braking mechanism 8. The numeral 14 shows a thread tension mechansim which is formed with an axle 15 having a female screw portion 15a and a tubular portion 15b at an upper part, and a male screw portion 15c at a lower part. A lower portion of the male screw portion is screwed into the machine frame 4. The thread tension mechanism is composed of the axle 15 fixed to the machine frame with a nut 16, a spring 17, an adjusting dial 18, a spring 19, a thread tension disc 22 secured to the axle 15 and a thread tension disc 20 with a screw 21. The thread tension disc 20 is formed with a pair of bendings 20a and 20b which moderately engage a tongue 22a of the thread tension disc 22 in order to almost decide orientation of the thread tension disc 20. As shown in FIG. 1, the suturing thread 2 passes along the inside of the bending 20a, and turns around the tubular portion 15b, and returns along the inside of the bending 20b, during which the suturing thread 2 is kept on the thread tension disc 22 biased upwardly by the thread tension disc 20 and the spring 19, and is effected with thread tension. The thread tension is adjusted by rotating operation of the adjusting dial 18 outside of the suturing instrument.

The numeral 23 is a shuttle holding member. A rod portion 24 passes through a pair of bent portions 4a of the machine frame 4 and slidably inserts into a pipe 26 fixed to the machine frame with a screw 25.

The rod portion 24 is formed with a guide groove 24a which is engaged with a rotation stopping pin 27 provided on the machine frame 4. A holder 28 is provided to the rod, and when the holder 28 is operated by pushing, a shuttle holder member 29 positioned in opposition to the holder is reciprocated in a certain range in restriction of rotation with respect to the machine fame 4. The numeral 50 is a stopping screw for restraining reciprocation of the shuttle holder 23. The shuttle holder member 29 is composed of a shuttle holder 30 and a shuttle claw 32 secured to the shuttle holder by a screw 31, and a shuttle 33 is held on the shuttle holder. The needle bar 34 is secured at its one end to a needle bar supporter 36 with a screw 37, the needle bar supporter 36 being secured to the machine frame 4 with screws 35. The needle bar 34 is provided on its other end with a thread guide piece 38 secured thereto by a screw 39, so that the curved needle 41 is detachably attached thereto. The curved needle 41 is, as shown in FIG. 3, formed with a needle eye 41a at its end portion and is formed with an oblong groove 41b for guiding the thread from a half way on the outer circumference of the curve to the needle eye 41a. With reference to FIG. 4, a main body 51 is composed of the machine frame 4 and the needle bar holder 36 provided to the machine frame. The main body is attached with the cover 7 by screws 42 and 43 and with the cover 12 by disc screws 44, 45 and 46.

A further reference will be made to operations of embodiments according to the present invention. Under condition that the cover 7 is taken off from the main body 51 prior to the suturing operation, and the operating portion 10a of the braker 10, the thread supply member 1 coiling the suturing thread 2 is mounted on the thread standing axis 6. With respect to the suturing thread 2, under mentioned steps are taken: passing the thread between the thread tension discs 20 and 22 of the thread tension mechanism 14 as shown in FIGS. 1, passing into the guide hole 38a of the guide piece 38 through the thread guide groove 36a, passing through the needle eye 41a along the oblong groove 41b formed on the outer circumference of the curved needle 41, drawing out the suturing thread from the needle eye in dependence upon the amount of suturing length, and combining to the thread hole 33a of the shuttle 33 at an end of the thread to make a suturing thread 47 at the shuttle side (hereinafter called as "shuttle thread"). The shuttle is supported between the shuttle holder 30 and the shuttle claw 32. Prior to penetration of the curved needle 41 into the human part to be treated, the shuttle 33 is moved toward to the main body 51 as well as the shuttle thread 47 is moved toward to the main body 51 to prevent obstacle to the penetration of the needle 41. With reference to FIGS. 5-12, it can be observed that when the curved needle 41 is penetrated into the parts 52 and 53 to be sutured from a penetrating hole 52a, the needle thread 54a pulled in straight as shown in FIG. 5 between the needle eye 41a and the penetrating hole 53a, is changed into a loop of crescent 54L of the needle thread together with the needle thread 54b guided in the oblong groove 41b. The shuttle 33 connected with the shuttle thread 47 is moved to a remote side from the main body 51 and is advanced into the needle thread loop 54L to catch this loop, and then if the shuttle 33 is returned to the main body 51, the shuttle 33 makes a round of the needle thread 54a, and the shuttle thread 47 crosses with the needle thread 54 as shown in FIG. 7.

The curved needle 41 is pulled out from the penetrating hole 52a, and the needle thread 54 and the shuttle thread 47 are tightened to form an initial stitch of lock stitch.

The penetration point is moved so that the curved needle 41 is caused to pass into the parts 52 and 53 to be sutured, and a needle thread loop 54L is formed as shown in FIG. 9. The shuttle 33 is reciprocated to cross, as shown in FIG. 10, the needle thread 54 and the shuttle thread 47, and the curved needle 41 is drawn out from the penetration hole 52'a, as shown in FIG. 11. The needle thread 54 and the shuttle thread 47 are tightened to form a stitch next to the lock stitch. The above mentioned operation is repeated and finally the needle thread 54 and the shuttle thread 47 are combined to form continuously suturing formation as shown in FIG. 12.

In the above suturing operation, the control of the thread supply member 1 is released when penetrating the curved needle 4' and when the curved needle 41 is drawn out from the penetrating position after crossing the needle thread 54 and the shuttle thread 47, and the thread is tightened by controlling the thread supply member. In this case, there are occasions that the thread tension by the thread tension mechanism 14 is weak or the needle thread 54 is supplied more than required by the operator's error. If the suturing were carried out in such a condition, the needle thread loop 54L would be loosened, and it would be difficult to catch the thread loop 54L by the shuttle 33, or reversely it would be difficult to perform the thread tightening in the preferable condition if the needle thread (54) were not be supplied as much as required.

A reference will be made to the optimum amount of supplying the thread in FIG. 11. With respect to a stitch to be formed after insertion of the curved needle 41, assuming the amount, as L, of supplying the needle thread 54 from the insertion hole 52'a of the stitch having already been formed after tightening the thread to the needle hole 41a, when the supply amount L is made equal to the stitching pitch P, it is the optimum amount of supplying the needle thread. According to the suturing instrument 3 of the invention, with respect to insertion of the curved needle 41 for forming a subsequent stitch in the course of the suturing process, if the supplying amount L of the needle thread 54 after tightening the thread is less than the stitching pitch P, the thread supplying member 1 is released from control and the suturing machine 3 is moved, thereby to adjust the supplying amount L at a suitable length, or reversely if the supplying amount L of the needle thread 54 is more than the stitching pitch P, the flange portion 1a is, in the present embodiment, rotated in the counterclockwise direction in FIG. 4 without releasing the thread supply member 1 from control, and when the needle thread 4 is turned in return, the supplying amount L may be adjusted to the proper length. Depending upon the suturing instrument 3 of the invention, adjustment of the supplying amount L of the needle thread 54 is an adjustment by operating the ratchet with sound as well as the visual observation of the supplying amount of the needle thread, that is, an adjustment supported by sense of eye, ear and sensitivity of the fingertips.

According to the present invention, the suturing thread combined to the shuttle and the suturing thread at the side of the curved needle are crossed to suture up the human part to be sutured characterized by controlling the suturing thread out of the suturing instrument, thereby to keep the suturing thread at proper amount, so that the stitching is made stable with high operationability.

It will be understood that each of the elements described above, or two or more together, may also find a useful application in other types of suturing instruments for surgical operations differing from the types described above.

While the invention has been illustrated and described as embodied in a suturing instrument, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific of this invention.

What is claimed as new and desired to be protected by Letters Patent is set forth in the appended claims.

1. A suturing instrument for surgical operations having a needle and a shuttle operated to form a needle thread and a shuttle thread supplied thereto and to interlock the needle thread and the shuttle thread so as to form lock stitches for suturing up a wound or an incision, the instrument comprising a housing having a frame; thread-supplying means including a turnable bobbin loaded with a suture-thread to be supplied to the needle and the shuttle; thread-supply control means including braking means mounted in said housing and normally pressed against said bobbin to prevent a turning movement thereof; and releasing means, said releasing means having an accessible part positioned outside of said housing, said thread-supply control means including a turnable flange mounted on said bobbin and partially extending outwards of the housing to be accessible to an operator, said flange having an outer circumference formed with a plurality of grooves; said braking means including a braking axle secured to said frame, a braker on said axle and having a portion turnably mounted in said housing and selectively engageable or disengageable in one of said grooves, and a spring normally pressing said portion against said flange, said releasing means being operated to displace said portion of said braker away from said flange to allow the turning movement of said flange and said bobbin therewith to permit the suture-thread to be drawn out from said bobbin during operation, or to displace said portion into engagement with one of said grooves to permit tightening of the suture-thread, said thread-supply control means and said releasing means being operative for adjusting the amount of the suture-thread supplied to the needle and the shuttle to a required stitching pitch so that if, after tightening, the supplied thread amount is less than the stitching pitch said flange is released by said releasing means from said braker and the bobbin is allowed to turn, and if the supplied thread amount is more than the stitching pitch, the flange is rotated by the operator in a counter direction without being released from said braker, thereby adjusting the supplied thread amount while the needle remains in the flesh.

2. The instrument of claim 1, further including thread-tension means in said housing and adapted to receive the suture-thread from said bobbin and supply it to the needle and the shuttle.

3. The instrument of claim 2, wherein said thread-tension means include a first thread tension disc formed with a pair of bent projections and a second thread tension disc having a tongue engageable with said projections.

4. The instrument of claim 3, wherein said thread-tension means further include a thread tension-adjusting dial coaxial with said first and second tension discs.

* * * * *